United States Patent

Lang

[11] 4,224,939
[45] Sep. 30, 1980

[54] BACTERIA-TIGHT SYSTEM FOR ARTIFICIAL RESPIRATION

[76] Inventor: Volker Lang, Spitzwegstrasse 63b, 8012 Ottobrunn, Fed. Rep. of Germany

[21] Appl. No.: 913,086

[22] Filed: Jun. 6, 1978

[30] Foreign Application Priority Data

Jun. 6, 1977 [DE] Fed. Rep. of Germany ........ 2725515

[51] Int. Cl.³ ............................................. A61M 17/00
[52] U.S. Cl. ........................... 128/205.13; 128/207.14
[58] Field of Search ............... 128/145.8, 145.6, 145.5, 128/188, 145.7, 351, 28, 30, 30.2, 205.13, 205.17, 204.18, 207.14, 204.28, 200.26

[56] References Cited

U.S. PATENT DOCUMENTS

| | | | |
|---|---|---|---|
| 3,434,471 | 3/1969 | Liston ................................ | 128/145.8 |
| 3,814,091 | 6/1974 | Henkin ........................... | 128/145.8 X |
| 3,815,596 | 6/1974 | Keener et al. ................ | 128/141 R X |
| 4,011,866 | 5/1977 | Klein et al. ........................ | 128/145.8 |

Primary Examiner—Harry N. Haroian
Attorney, Agent, or Firm—Fleit & Jacobson

[57] ABSTRACT

An appliance for establishing a bacteriologically safe connection between a respirator and an endotracheal tube comprises a head fitting, which is adapted to be mounted on the endotracheal tube. A flexible tube for supplying inhalable gas and a flexible withdrawing tube for withdrawing exhaled air are connected to said head fitting. An exhalation valve is incorporated in the withdrawing tube and is incorporated by a controller in step with the artificial respiration. An inflatable bag, which is manually operable to effect artificial respiration, is connected by a tee fitting to the supply tube, which is connected by a bacteria filter and the controller to the respirator. The inflatable bag is provided with a sensor, which is connected by a signal line to the controller and causes the latter to close and open the exhalation valve in step with the manually effected artificial respiration.

11 Claims, 1 Drawing Figure

Bacteriological Safety Provided by Sealed Universal System for Artificial Respiration

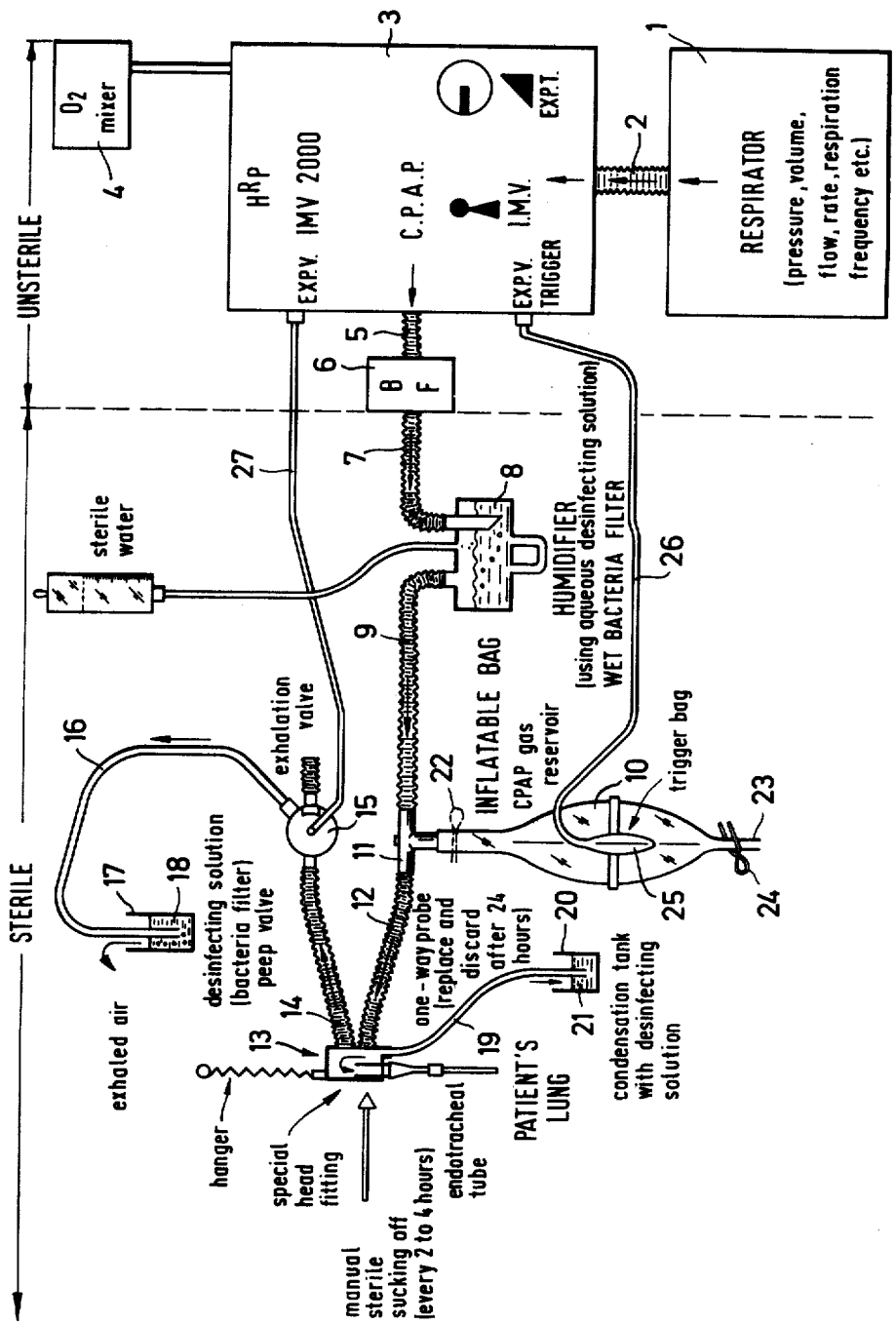

BACTERIA-TIGHT SYSTEM FOR ARTIFICIAL RESPIRATION

This invention relates to an appliance for establishing a bacteriologically safe connection between a respirator and an endotracheal tube.

Conventional respirators are connected to the trachea of a patient by flexible tubing and an endotracheal tube. The patient is induced to breathe in that his lung is inflated by the inhalable gas supplied during the inhalation phase and his lung is passively emptied during the exhalation phase by collapsing owing to its elasticity.

Artificial respiration effected by known respirators involves the disadvantage that germs and bacteria can enter the patient's lung with the inhaled air and may give rise to pneumonia. Recent U.S. statistics have shown that a mortality of up to 70% must be expected with adults suffering from pneumonia after artificial respiration. This is not surprising in view of the progressive increase in resistance of hospital germs to antibiotics.

It is a primary object of the invention to provide for artificial respiration a system which has a high bacteriological safety. Besides, it is desired to maintain a relatively high relative humidity of the inhalable gases without a formation of droplets at a temperature of 36° to 37° C., to preclude a restriction in the use of various artificial respiration techniques and ancillary measures and of various respirators, to preclude a restriction in use owing to the patient's age, and to provide for artificial respiration a system which distinguishes by high technical safety and high economy.

In an appliance of the kind described first hereinbefore, the object set forth is accomplished according to the invention in that a head fitting is provided, which is adapted to be mounted on the endotracheal tube, a flexible supply tube for supplying inhalable gas and a flexible withdrawing tube for withdrawing exhaled air are connected to said head fitting, an exhalation valve is incorporated in the withdrawing tube and is operated by a controller in step with the artificial respiration, an inflatable bag, which is manually operable to effect artificial respiration, is connected by a tee fitting to the supply tube, the latter is connected by a bacteria filter and a controller to the respirator, and the inflatable bag is provided with a sensor, which is connected by a signal line to the controller and causes the latter to close and open the exhalation valve in step with the manually effected artificial respiration. The invention provides for artificial respiration a sealed system which ensures an optimum bacteriological safety. Inhalable gas flows from the respirator through the controller and a bacteria filter into a sealed system, which comprises the flexible tubes and which is protected against an ingress of germs which may be detrimental to the patient. Bacteriological safety will be provided by the appliance according to the invention even when the head fitting must be removed from the endotracheal tube in intervals of about two to four hours to permit the tracheal secretion to be sucked off. In the patient, this clearing of the bronchi results in a certain oxygen deficiency, which initiates spontaneous breathing. Because the patient must again be accustomed to the rhythm of the respirator after the clearing of the bronchi, the artificial respiration is usually resumed by the maximal operation of an inflatable bag and the operation of the respirator is not initiated until the patient's breathing rhythm agrees with the rhythm of the respirator. Unsterile air could be supplied to the patient particularly during such manual effected artificial respiration and would increase the risk of pneumonia. Because the inflatable bag is included in the appliance according to the invention, the bacteriological safety of the sealed system for artificial respiration is maintained also during the adaptation of the patient after the clearing of the bronchi. Where the system according to the invention is used, the head fitting is fitted on the endotracheal tube when the bronchi have been cleared and the patient is then subjected to artificial respiration in that the inflatable bag is operated to supply the patient with air which has flown through the respirator, the controller and the bacteria filter. In response to the manual operation of the bag, a sensor connected to said bag delivers signal to the controller so that the latter can close and open the exhalation valve in step with the artificial respiration.

The withdrawing tube is also connected to a bacteria filter so that germs from the patient cannot escape into the environment and germs from the environment cannot enter the withdrawing tube.

In a particularly preferred embodiment of the invention, a sealed conditioner for humidifying and warming up the inhalable gas is incorporated in the supply tube between the bacteria filter and the inflatable bag. That conditioner may consist of a known, sealed vessel, which is adapted to be inserted into a unit for manual and automatic control and which holds the humidifying liquid and carries a connecting pipe for receiving gas which is to be humidified and warmed up and a connecting pipe for delivering the conditioned gas. Baffles for deflecting and thoroughly mixing the gas with the humidifying liquid are contained in the interior of the vessel. The latter is provided on its underside with an extension, which contains metal plates, which when the container has been inserted into the unit for manual and automatic control enclose an iron core and constitute a short-circuit secondary winding of a transformer so that the plates are induction-heated.

In the conditioner, the gas flows suitably through sterile water, which contains an aqueous, non-evaporating disinfecting solution. Because the bacteria filter has only an effectiveness of 99.8%, the final sterilization is effected in the conditioner so that only sterile gas is supplied to the patient.

The inflatable bag consists suitably of transparent plastic material so that a formation of condensate will be apparent from the outside. Such condensate can be drained from the inflatable bag through a tubular tail portion, which is normally sealed by a clip.

According to a further preferred feature of the invention, a trigger bag is detachably secured to the inflatable bag and is connected by a flexible tube to the controller. That trigger bag constitutes a simple sensor, which can be repeatedly used.

If the inhalable air were humidified and warmed up in known systems for artificial respiration, it would be difficult to supply inhalable gas to the patient at the correct temperature regardless of the rate at which inhalable gas is required at any time. In this connection, the temperature drop in the conduit for the inhalable gas which has been warmed up must be taken into account. That temperature drop depends on the rate of such gas. A human adult requires about 8 to 15 liters of inhalable gas per minute. Gas which is inhaled at that rate and has been heated to 50° C. will undergo a temperature drop of about 12° C. untuil it has reached the endotracheal tube. On the other hand, a newly born infant requires only 1 to 2 liters of inhalable air per minute. Air inhaled at such a low rate will undergo a temperature drop of about 20° C.

For this reason it is a further object of the present invention to supply a patient in a simple manner with inhalable gas at the proper temperature, regardless of the patient's age and the rate at which he requires inhalable gas.

This further object is accomplished according to a further feature of the invention in that the controller communicates with an additional source of inhalable gas and continuously supplies inhalable gas at a high rate to the supply tube during the exhalation phase. As a result, a flow of inhalable gas at a relatively high rate is maintained during the exhalation phase and the temperature drop in the inhalable gas from the conditioner to the connector head is substantially constant so that the inhalable gas is at a substantially constant temperature regardless of the rate at which inhalable gas is required by the patient. The rate at which inhalable gas flows throughout the exhalation phase is selected so that the temperature fluctuations in the inhalable gas will be very small even if the rate of inhalable gas is increased further. As a result, the temperature of the inhalable gas remains within permissible limits, regardless of the rate at which inhalable gas is required during the inhalation phase.

The system according to the invention is preferably designed to be discarded after a single use so that a complicated cleaning after use is not required and the bacteriological safety is increased. The system according to the invention is marketed in sterile bag packages.

Another important advantage resides in that the controller permits of a connection of the appliance according to the invention to conventional respirators so that a universal use is ensured.

Further desirable features of the appliance according to the invention will be recited more fully in the subclaims.

An embodiment of the appliance according to the invention will now be described by way of example with reference to the single FIGURE of the drawing, in which the system for artificial respiration is shown diagrammatically.

A respirator 1 of usual type is connected by a flexible tube 2 to a controller-adapter unit 3. The controller 3 is connected by a conduit to another source 4 of inhalable air. The controller 3 is connected by a flexible tube 5 to a bacteria filter 6, from which a flexible tube 7 leads to a vessel 8, which is filled with sterile water at elevated temperature. The inhalable air flows through said water. Because water is evaporated in the vessel 8, sterile make-up water must be continuously supplied to said vessel from a supply vessel through a flexible tube.

The vessel 8 is connected by sections 9, 12 of a flexible supply tube to a head fitting 13, which is adapted to be mounted on the endotracheal tube. The tube sections 9, 12 are interconnected by a tee fitting 11, which is connected to an inflatable bag 10. During normal operation, the inflatable bag is sealed by a hose clip 22. The bag 10 has a tubular tail 23, which is sealed by a hose clip 24.

A flexible withdrawing tube 14 leads from the head fitting 13 to the exhalation valve 15, which is connected by a flexible tube 16 to a bacteria filter. The latter comprises a vessel 17, which is partly filled with disinfecting solution 18. A flexible tube 19 is connected to the head fitting 13 and serves to withdraw condensate to a vessel 20, which is partly filled with disinfecting solution 21.

A trigger bag 25 is detachably connected to the inflatable bag 10 and through a flexible tube 26 communicates with the controller 3. The controller 3 is connected to the exhalation valve by a control conduit 27. When the trigger bag is compressed in the inhalation phase of artificial respiration which is manually effected by the inflatable bag, the controller 3 closes the exhalation valve so that the respirator can build up the pressure which is required for the artificial respiration of the patient.

Any condensate will be automatically forced out of the head fitting under the pressure of the inhalable air.

When the patient is subjected to artificial respiration which is manually effected, the conditioner acts as a check valve.

The unsterile part of the system is apparent from the right-hand part of the drawing. It consists of the respirator 1, which may be pressure- or volume- or flow rate-controlled, and the controller-adapter unit 3. The controller 3 can be connected to the respirator in a very simple manner without need for alterations so that up-to-date artificial respiration techniques can be carried out with existing respirators, which have proved to be reliable, when such respirators are provided with the appliance according to the invention. The unit 3 serves also as a universal adapter so that the universal system for artificial respiration shown on the left side of the drawing can be connected to any respirator. This standardization obviously greatly reduces the expenditure involved in artificial respiration.

The mode of operation of the system for artificial respiration will now be explained briefly. Unsterile inhalable gas which is delivered by the respirator 1 flows through the controller 3 to the commercially available dry bacteria filter 6, as indicated by arrows. Gas which is substantially free from bacteria flows from the filter 6 into the flexible tube system for artificial respiration. That system may be designed for a single use or as a steam-sterilizable system for repeated use. The humidifier 8 consists of an evaporator and can be supplied with sterile water in a simple manner by an infusion device during artificial respiration. A disinfectant, such as Rivanol solution, is added to the water to ensure that any bacteria which have passed through the bacteria filter 6 will be intercepted and destroyed. Thus, the conditioner serves not only to warm up and humidify the inhalable gas but also as a wet bacteria filter. Sterile inhalable gas flows through the corrugated tube 9 to the tee fitting 11, which carries an inflatable bag 10. The latter serves also as a gas reservoir. From the tee fitting 11, the inhalable gas flows to the head fitting 13, which is provided with an automatic condensate trap. By means of a one-way probe 19, which is replaced after 24 hours and subsequently discarded, condensate is conducted into a small vessel 20, which contains a disinfecting solution. For this reason it is not necessary to open the system for that purpose. Such opening would involve a risk of bacterial contamination. Because the inhalable gas has been conditioned to optimum temperature and humidity conditions (100% relative humidity at the body temperature of 36° to 37° C.), it is not necessary to rinse the tracheal tube and it is sufficient to suck the trachea in intervals of two to four hours. A manually effected artificial respiration has proved to be highly valuable particularly after the clearing of the bronchi of a schoolchild and of an adult and should not require an opening of the sterile system. For this reason the inflatable bag which is incorporated in the system for artificial respiration carries an external trigger bag, which is compressed with the inflatable bag 10 when the same is manually operated. In response to the compression of the trigger bag, the controller 3 controls the exhalation valve 15 in phase. As indicated by arrows, the air which has been exhaled by the patient flows through the withdrawal tube 14 to the exhalation valve 15. Any desired positive exhalation pressure can be adjusted in a simple manner in that the withdrawal tube is submerged to different depths into the disinfecting solution 18.

What is claimed is:

1. An appliance for establishing a bacteriologically safe connection between a respirator used in artificial respiration and an endotracheal tube, comprising a head fitting adapted to be mounted on the endotracheal tube; flexible supply tube means for supplying inhalable gas; flexible withdrawing tube means for withdrawing exhaled air, said tube means being connected to said head fitting; and exhalation valve incorporated in the withdrawing tube means; an inflatable bag manually operable to effect artificial respiration; a controller in step with the artificial respiration for controlling said exhalation valve; a tee fitting for connecting said inflatable bag to the supply tube means; a bacteria filter positioned in said supply tube means, said controller connecting said supply tube means to the respirator, the inflatable bag being provided with a sensor; first signal means for connecting the sensor to the connector; and second signal means for connecting the controller to the exhalation valve so that said controller closes and opens the exhalation valve in step with pressure changes resulting from the manually effected artificial respiration.

2. An appliance as set forth in claim 1, characterized in that a sealed conditioner for humidifying and warming up an inhalable gas is incorporated in the supply tube means between the bacteria filter and the inflatable bag.

3. An appliance as set forth in claim 2, characterized in that the conditioner contains sterile water and a non-evaporating, aqueous disinfecting solution and is flown through by the inhalable gas.

4. An appliance as set forth in claim 1, characterized in that the inflatable bag consists of transparent plastic material and is provided at its outlet with a hose clip.

5. An appliance as set forth in claim 1, characterized in that said sensor comprises a trigger bag detachably secured to the inflatable bag and in that said first signal means comprises a flexible tube connected to the controller.

6. An appliance as set forth in claim 1, characterized in that the head fitting has three connecting pipes, the supply and withdrawing tube means being connected to respective ones of said connecting pipes, and the third connecting pipe being adapted to be fitted on the endotracheal tube.

7. An appliance as set forth in claim 1, characterized in that the head fitting is pot-shaped and is provided in its bottom with an outlet; said appliance further comprising a flexible tube connected to said outlet for withdrawing condensate, which has accumulated in the head fitting, and a condensate vessel, which is filled with disinfecting solution, for receiving condensate from said flexible tube.

8. An appliance as set forth in claim 1, characterized in that the exhalation valve consists of a baloon valve, and said second signal means comprises a flexible tube connecting said baloon valve to the controller.

9. An appliance as set forth in claim 1, characterized in that the controller has an inlet, which is adapted to be connected to any respirator.

10. An appliance as set forth in claim 1, characterized in that the apparatus includes another source of inhalable gas connected to the controller for continuously supplying inhalable gas at a high rate to the supply tube means during an exhalation phase.

11. An appliance as set forth in claim 10, characterized in that the inhalable gas flows during the exhalation phase at such a high volume rate that a temperature drop in the inhalable gas from the conditioner to the head fitting remains substantially constant regardless of the rate at which inhalable gas is required by the patient.

* * * * *